(12) United States Patent
Saxena et al.

(10) Patent No.: US 9,193,779 B2
(45) Date of Patent: Nov. 24, 2015

(54) RECOMBINANT HUMAN FIBRONECTIN FRAGMENT FOR CELL CULTURE

(71) Applicant: Corning Incorporated, Corning, NY (US)

(72) Inventors: Deepa Saxena, Framingham, MA (US); Himabindu Nandivada, Cambridge, MA (US)

(73) Assignee: Corning Incorporated, Corning, NY (US)

( * ) Notice: Subject to any disclaimer, the term of this patent is extended or adjusted under 35 U.S.C. 154(b) by 131 days.

(21) Appl. No.: 13/837,207

(22) Filed: Mar. 15, 2013

(65) Prior Publication Data

US 2014/0120616 A1 May 1, 2014

Related U.S. Application Data

(60) Provisional application No. 61/719,216, filed on Oct. 26, 2012.

(51) Int. Cl.
| | |
|---|---|
| *C12N 5/09* | (2010.01) |
| *C07K 14/78* | (2006.01) |
| *C12N 5/0735* | (2010.01) |
| *C12N 5/0775* | (2010.01) |
| *C12N 5/074* | (2010.01) |
| *C12N 5/00* | (2006.01) |

(52) U.S. Cl.
CPC .............. *C07K 14/78* (2013.01); *C12N 5/0037* (2013.01); *C12N 5/0606* (2013.01); *C12N 5/0663* (2013.01); *C12N 5/0675* (2013.01); *C12N 5/0693* (2013.01); *C12N 5/0696* (2013.01)

(58) Field of Classification Search
None
See application file for complete search history.

(56) References Cited

U.S. PATENT DOCUMENTS

| | | | |
|---|---|---|---|
| 4,578,079 | A | 3/1986 | Ruoslahti et al. |
| 4,589,881 | A | 5/1986 | Pierschbacher et al. |
| 5,171,318 | A | 12/1992 | Gibson et al. |
| 2008/0131425 | A1 | 6/2008 | Garcia et al. |
| 2010/0021998 | A1* | 1/2010 | Sanyal et al. ................. 435/366 |

FOREIGN PATENT DOCUMENTS

| | | |
|---|---|---|
| EP | 2147971 A2 | 1/2008 |
| WO | 89/01942 A1 | 3/1989 |
| WO | 92/09200 A1 | 6/1992 |

OTHER PUBLICATIONS

Uniprot ("Fibronectin, *Homo sapeins*" downloaded from http://www.uniprot.org/blast/?about=P0275111[1176-1266]&key=Domain on Nov. 19, 2014)).*
Hochuli et al (Nature Biotechnology (1988) 6 (11 ): 1321-1325).*
Uchida et al (The Prostate (2005) 66: 536-545).*
Cutler and Garcia, Biomaterials, 24:1759-1770 (2003).
Extended European Search Report EP 11 19 1960 mailed Mar. 26, 2012.
International Search Report of International Application No. PCT/US2013/066138 dated Jan. 7, 2014.
Kimizuka, F. et al.; Production and Characterization of Functional Domains of Human Fibronectin Expressed in *Escherichia coli*; J. Biochem. vol. 110, pp. 284-291 (1991).

* cited by examiner

*Primary Examiner* — Marcela M Cordero Garcia
*Assistant Examiner* — Mindy Newman
(74) *Attorney, Agent, or Firm* — Hoffman & Baron, LLP (57) ABSTRACT

The present invention discloses protein fragment including a cell binding region of fibronectin and methods of using the same for cell culture. Additionally, surfaces modified with such protein fragment and compositions including the same are provided. Desirably, such surfaces allow various cells to adhere thereto yet avoid issues associated with animal-derived products.

15 Claims, 6 Drawing Sheets

SEQUENCE LISTING

<160> NUMBER OF SEQ ID NOS: 3

<210> SEQ ID NO 1
<211> LENGTH: 368
<212> TYPE: PRT
<213> ORGANISM: Homo sapiens

<400> SEQUENCE: 1

```
Pro Leu Ser Pro Pro Thr Asn Leu His Leu Glu Ala Asn Pro Asp Thr
 1               5                  10                  15

Gly Val Leu Thr Val Ser Trp Glu Arg Ser Thr Thr Pro Asp Ile Thr
            20                  25                  30

Gly Tyr Arg Ile Thr Thr Thr Pro Thr Asn Gly Gln Gln Gly Asn Ser
        35                  40                  45

Leu Glu Glu Val Val His Ala Asp Gln Ser Ser Cys Thr Phe Asp Asn
    50                  55                  60

Leu Ser Pro Gly Leu Glu Tyr Asn Val Ser Val Tyr Thr Val Lys Asp
65                  70                  75                  80

Asp Lys Glu Ser Val Pro Ile Ser Asp Thr Ile Ile Pro Ala Val Pro
                85                  90                  95

Pro Pro Thr Asp Leu Arg Phe Thr Asn Ile Gly Pro Asp Thr Met Arg
            100                 105                 110

Val Thr Trp Ala Pro Pro Pro Ser Ile Asp Leu Thr Asn Phe Leu Val
        115                 120                 125

Arg Tyr Ser Pro Val Lys Asn Glu Glu Asp Val Ala Glu Leu Ser Ile
    130                 135                 140

Ser Pro Ser Asp Asn Ala Val Val Leu Thr Asn Leu Leu Pro Gly Thr
145                 150                 155                 160

Glu Tyr Val Val Ser Val Ser Ser Val Tyr Glu Gln His Glu Ser Thr
                165                 170                 175

Pro Leu Arg Gly Arg Gln Lys Thr Gly Leu Asp Ser Pro Thr Gly Ile
            180                 185                 190

Asp Phe Ser Asp Ile Thr Ala Asn Ser Phe Thr Val His Trp Ile Ala
        195                 200                 205

Pro Arg Ala Thr Ile Thr Gly Tyr Arg Ile Arg His His Pro Glu His
    210                 215                 220

Phe Ser Gly Arg Pro Arg Glu Asp Arg Val Pro His Ser Arg Asn Ser
225                 230                 235                 240

Ile Thr Leu Thr Asn Leu Thr Pro Gly Thr Glu Tyr Val Val Ser Ile
                245                 250                 255

Val Ala Leu Asn Gly Arg Glu Glu Ser Pro Leu Leu Ile Gly Gln Gln
            260                 265                 270

Ser Thr Val Ser Asp Val Pro Arg Asp Leu Glu Val Val Ala Ala Thr
        275                 280                 285

Pro Thr Ser Leu Leu Ile Ser Trp Asp Ala Pro Ala Val Thr Val Arg
    290                 295                 300

Tyr Tyr Arg Ile Thr Tyr Gly Glu Thr Gly Gly Asn Ser Pro Val Gln
305                 310                 315                 320

Glu Phe Thr Val Pro Gly Ser Lys Ser Thr Ala Thr Ile Ser Gly Leu
                325                 330                 335

Lys Pro Gly Val Asp Tyr Thr Ile Thr Val Tyr Ala Val Thr Gly Arg
            340                 345                 350

Gly Asp Ser Pro Ala Ser Ser Lys Pro Ile Ser Ile Asn Tyr Arg Thr
        355                 360                 365
```

<210> SEQ ID NO 2
<211> LENGTH: 6
<212> TYPE: PRT
<213> ORGANISM: Artificial Sequence
<220> FEATURE:
<223> OTHER INFORMATION: histidine tag

<400> SEQUENCE: 2

His His His His His His
1               5

<210> SEQ ID NO 3
<211> LENGTH: 375
<212> TYPE: PRT
<213> ORGANISM: Artificial Sequence
<220> FEATURE:
<223> OTHER INFORMATION: R2 peptide

<400> SEQUENCE: 3

Met His His His His His Pro Leu Ser Pro Thr Asn Leu His
1               5                   10                  15

Leu Glu Ala Asn Pro Asp Thr Gly Val Leu Thr Val Ser Trp Glu Arg
            20                  25                  30

Ser Thr Thr Pro Asp Ile Thr Gly Tyr Arg Ile Thr Thr Pro Thr
        35                  40                  45

Asn Gly Gln Gln Gly Asn Ser Leu Glu Val Val His Ala Asp Gln
50                      55                  60

Ser Ser Cys Thr Phe Asp Asn Leu Ser Pro Gly Leu Glu Tyr Asn Val
65                  70                  75                  80

Ser Val Tyr Thr Val Lys Asp Lys Glu Ser Val Pro Ile Ser Asp
                85                  90                  95

Thr Ile Ile Pro Ala Val Pro Pro Thr Asp Leu Arg Phe Thr Asn
            100                 105                 110

Ile Gly Pro Asp Thr Met Arg Val Thr Trp Ala Pro Pro Ser Ile
            115                 120                 125

Asp Leu Thr Asn Phe Leu Val Arg Tyr Ser Pro Val Lys Asn Glu Glu
    130                 135                 140

Asp Val Ala Glu Leu Ser Ile Ser Pro Ser Asp Asn Ala Val Val Leu
145                 150                 155                 160

Thr Asn Leu Leu Pro Gly Thr Glu Tyr Val Val Ser Val Ser Ser Val
                165                 170                 175

Tyr Glu Gln His Glu Ser Thr Pro Leu Arg Gly Arg Gln Lys Thr Gly
            180                 185                 190

Leu Asp Ser Pro Thr Gly Ile Asp Phe Ser Asp Ile Thr Ala Asn Ser
        195                 200                 205

Phe Thr Val His Trp Ile Ala Pro Arg Ala Thr Ile Thr Gly Tyr Arg
    210                 215                 220

Ile Arg His His Pro Glu His Phe Ser Gly Arg Pro Arg Glu Asp Arg
225                 230                 235                 240

Val Pro His Ser Arg Asn Ser Ile Thr Leu Thr Asn Leu Thr Pro Gly
                245                 250                 255

Thr Glu Tyr Val Val Ser Ile Val Ala Leu Asn Gly Arg Glu Glu Ser
            260                 265                 270

Pro Leu Leu Ile Gly Gln Gln Ser Thr Val Ser Asp Val Pro Arg Asp
        275                 280                 285

Leu Glu Val Val Ala Ala Thr Pro Thr Ser Leu Leu Ile Ser Trp Asp
    290                 295                 300

| | | | | | | | | | | | |
|---|---|---|---|---|---|---|---|---|---|---|---|
| Ala | Pro | Ala | Val | Thr | Val | Arg | Tyr | Tyr | Arg | Ile | Thr | Tyr | Gly | Glu | Thr |
| 305 | | | | 310 | | | | 315 | | | | | 320 |
| Gly | Gly | Asn | Ser | Pro | Val | Gln | Glu | Phe | Thr | Val | Pro | Gly | Ser | Lys | Ser |
| | | | 325 | | | | | 330 | | | | | 335 |
| Thr | Ala | Thr | Ile | Ser | Gly | Leu | Lys | Pro | Gly | Val | Asp | Tyr | Thr | Ile | Thr |
| | | | 340 | | | | | 345 | | | | | 350 |
| Val | Tyr | Ala | Val | Thr | Gly | Arg | Gly | Asp | Ser | Pro | Ala | Ser | Ser | Lys | Pro |
| | | 355 | | | | | 360 | | | | | 365 |
| Ile | Ser | Ile | Asn | Tyr | Arg | Thr |
| 370 | | | | | 375 |

RECOMBINANT HUMAN FIBRONECTIN FRAGMENT FOR CELL CULTURE

CROSS-REFERENCE TO RELATED APPLICATION

This application claims priority to U.S. Provisional Patent Application No. 61/719,216, filed on Oct. 26, 2012, the entire contents of which are incorporated by reference herein.

FIELD OF THE INVENTION

The present invention relates to protein fragment and surfaces modified therewith which provide cell attachment for various cells.

BACKGROUND OF THE INVENTION

Extracellular matrix (ECM) protein coated surfaces have been widely used in cell culture. In particular, fibronectin is a commonly used ECM protein used in cell culture that supports cell attachment. ECM proteins used for coating surfaces for cell culture are generally of human or other animal origin and often poorly defined. The use of such ECM proteins can be problematic, for example, in human therapeutic applications where having a defined and animal-free culture is desirable. Thus, there is a need for better defined and animal-component free surfaces that support cell attachment for cell culture.

SUMMARY OF THE INVENTION

The present invention provides protein fragment including at least a cell binding region of fibronectin and surfaces wherein at least a portion thereof is modified with such protein fragment. Advantageously, surfaces modified with such protein fragment support cell attachment yet avoid issues associated with animal-derived products which are poorly defined and/or may elicit an immune response in therapeutic applications. Additionally, the present invention provides cell culture vessels and methods of culturing cells including a surface modified with a protein fragment of the present invention.

In one aspect, the present invention provides methods of culturing cells using a surface wherein at least a portion of the surface is modified with a protein fragment including amino acid sequence PLS PPTNLHLEAN PDTGVLTVSW ERSTTPDITG YRITTTPTNG QQGNSLEEVV HADQSSCTFD NLSPGLEYNV SVYTVKDDKE SVPISDTIIP AVPPPTDLRF TNIGPDTMRV TWAPPPSIDL TNFLVRYSPV KNEEDVAELS ISPSDNAVVL TNLLPGTEYV VSVSSVYEQH ESTPLRGRQK TGLDSPTGID FSDITANSFT VHWIAPRATI TGYRIRHHPE HFSGRPREDR VPHSRNSITL TNLTPGTEYV VSIVALNGRE ESPLLIGQQS TVSDVPRDLE VVAATPTSLL ISWDAPAVTV RYYRITYGET GGNSPVQEFT VPGSKSTATI SGLKPGVDYT ITVYAVTGRG DSPASSKPIS INYRT (SEQ ID NO: 1).

In one embodiment, the cells are cultured in serum-free media.

In one embodiment, the cells are derived from a human.

In one embodiment, the protein fragment further comprises a purification tag. In one embodiment, the purification tag comprises a histidine tag having 5-10 histidines (e.g., amino acid sequence HHHHHH (SEQ ID NO: 2)).

In embodiments, the cells are LNCaP cells, mesenchymal cells, bone marrow-derived human mesenchymal stem cells, embryonic stem cells or induced pluripotent stem cells. In an embodiment, the cells are human embryonic stem cells such as human embryonic stem cell line H9.

In another aspect, the present invention provides a protein fragment including amino acid sequence MHHHHHHPLS PPTNLHLEAN PDTGVLTVSW ERSTTPDITG YRITTTPTNG QQGNSLEEVV HADQSSCTFD NLSPGLEYNV SVYTVKDDKE SVPISDTIIP AVPPPTDLRF TNIGPDTMRV TWAPPPSIDL TNFLVRYSPV KNEEDVAELS ISPSDNAVVL TNLLPGTEYV VSVSSVYEQH ESTPLRGRQK TGLDSPTGID FSDITANSFT VHWIAPRATI TGYRIRHHPE HFSGRPREDR VPHSRNSITL TNLTPGTEYV VSIVALNGRE ESPLLIGQQS TVSDVPRDLE VVAATPTSLL ISWDAPAVTV RYYRITYGET GGNSPVQEFT VPGSKSTATI SGLKPGVDYT ITVYAVTGRG DSPASSKPIS INYRT (SEQ ID NO: 3).

In one embodiment, the present invention provides a surface wherein at least a portion of the surface is modified with a protein fragment including amino acid sequence SEQ ID NO: 3. In one embodiment, the surface is comparable to or exceeds one or more functional characteristics of a fibronectin coated surface. In one embodiment, the fibronectin coated surface includes fibronectin of human-origin.

In one embodiment, the present invention provides compositions including a surface modified with a protein fragment including the amino acid sequence SEQ ID NO: 3. In one embodiment, the composition is a cell culture vessel or microcarrier. In one embodiment, the cell culture vessel is a dish, a flask, a multi-well plate, or a microscopic slide.

In another aspect, the present invention provides methods of culturing cells using a surface wherein at least a portion of the surface is modified with a protein fragment including amino acid sequence MHHHHHHPLS PPTNLHLEAN PDTGVLTVSW ERSTTPDITG YRITTTPTNG QQGNSLEEVV HADQSSCTFD NLSPGLEYNV SVYTVKDDKE SVPISDTIIP AVPPPTDLRF TNIGPDTMRV TWAPPPSIDL TNFLVRYSPV KNEEDVAELS ISPSDNAVVL TNLLPGTEYV VSVSSVYEQH ESTPLRGRQK TGLDSPTGID FSDITANSFT VHWIAPRATI TGYRIRHHPE HFSGRPREDR VPHSRNSITL TNLTPGTEYV VSIVALNGRE ESPLLIGQQS TVSDVPRDLE VVAATPTSLL ISWDAPAVTV RYYRITYGET GGNSPVQEFT VPGSKSTATI SGLKPGVDYT ITVYAVTGRG DSPASSKPIS INYRT (SEQ ID NO: 3).

In one embodiment, the cells are derived from a human. In one embodiment, the cells are embryonic stem cells. In one embodiment, the cells are human embryonic stem cells. In one embodiment, the cells are LNCaP cells. In one embodiment, the cells are bone marrow-derived human cells. In one embodiment, the cells are human embryonic cell line H9. In one embodiment, the cells are induced pluripotent stem cells. In one embodiment, cells are cultured in serum-free media.

In one embodiment, the cells exhibit comparable or improved cell attachment as compared to a surface coated with fibronectin of human-origin.

These and other features of the invention will be better understood through a study of the following detailed description.

DETAILED DESCRIPTION OF THE INVENTION

As used herein the following terms shall have the definitions set forth below.

As used herein, the phrase "one or more functional characteristics of a fibronectin coated surface" includes, but is not limited to, cell attachment, growth, migration and differentiation. In one embodiment, one or more functional characteristics of a fibronectin coated surface are characterized using LNCaP cells. In another embodiment, one or more functional characteristics of a fibronectin coated surface are characterized using bone marrow-derived human mesenchymal stem cells. In yet another embodiment, one or more functional characteristics of a fibronectin coated surface are characterized using induced pluripotent stem cells. In still yet another embodiment, one or more functional characteristics of a fibronectin coated surface are characterized using human embryonic cell line H9 cells. Desirably, the surface is comparable to or exceeds cell attachment of a fibronectin coated surface.

As used herein, the phrase "comparable to or exceeds" with regard to the comparison of a cell culture surface coated with a compound of the present invention with a cell culture surface coated with fibronectin refers to the relative similarity or improvement in one or more functional characteristics being assessed. Desirably, quantification thereof would reveal at least 90% similarity in at least one functional characteristic.

As used herein, the phrase "purification tag" refers to a moiety that facilitates purification of a biological material, such as a protein fragment. Exemplary purification tags include a histidine-tag which includes 5-10 histidines. In one embodiment, the purification tag is a histidine-tag having amino acid sequence HHHHHH (SEQ ID NO: 2).

Fibronectin is a high-molecular weight (~440 kDa) ECM glycoprotein that binds to membrane-spanning receptor proteins called integrins as well as ECM components collagen, fibrin and heparan sulfate proteoglycans (e.g., syndecans). Fibronectin supports cell attachment, growth, migration and differentiation and has been shown to play a key role in wound healing, embryonic development and certain types of carcinogenesis.

Structurally, fibronectin exists as a dimer, consisting of two nearly identical polypeptide fragment chains linked by a pair of C-terminal disulfide bonds. Each fibronectin monomer has a molecular weight of 230-250 kDa and contains three types of modules: type I, II, and III. The modules are arranged into several functional and protein-binding domains along the length of a fibronectin monomer. There are four fibronectin-binding domains, allowing fibronectin to associate with other fibronectin molecules. One of these fibronectin-binding domains, $I_{1-5}$, is referred to as the "assembly domain", and it is required for the initiation of fibronectin matrix assembly. Modules $III_{8-10}$ correspond to the "cell-binding domain" of fibronectin. The RGD sequence (Arg-Gly-Asp) is located in $III_{10}$ and is the site of cell attachment via $\alpha5\beta1$ and $\alpha V\beta3$ integrins on the cell surface. The "synergy site" is in $III_9$ and has a role in modulating fibronectin's association with $\alpha5\beta1$ integrins. Fibronectin also contains domains for fibrin-binding ($I_{1-5}$, $I_{10-12}$), collagen-binding ($I_{6-9}$), fibulin-1-binding ($III_{13-14}$), heparin-binding and syndecan-binding ($III_{12-14}$).

Though not meant to be limited by any theory with the subject invention, the protein fragment of the present invention includes a recombinant fibronectin fragment wherein regions therein are believed to interact with one another in a manner that provides one or more functional characteristics of fibronectin. In particular, surfaces coated with such protein fragment are comparable to or exceed cell attachment of a human-origin fibronectin coated surface.

The protein fragment of the present invention may be produced using conventional recombinant technologies. Similarly, such protein fragment may be purified using conventional techniques to a degree suitable for a given application.

It is understood that one of skill in the art could substitute one or more amino acids of the protein fragment described herein without compromising the ability of the resultant protein fragment when coated on a surface to support cell culture.

In particular, protein fragment of the present invention may have conservative substitution of one or more amino acids. A conservative substitution being defined as the side chain of the respective amino acid being replaced by a side chain of similar chemical structure and polarity, the side chain being derived from a genetically coded or not genetically coded amino acid. Families of amino acids of this kind having similar side chains are known in the art. They comprise for instance amino acids having basic side chains (lysine, arginine, histidine), acidic side chains (aspartic acid, glutamic acid), uncharged polar side chains (glycine, asparagine, glutamine, serine, threonine, tyrosine, cysteine), non-polar side chains (alanine, valine, leucine, isoleucine, proline, phenylalanine, methionine, tryptophan), beta-branched side chains (threonine, valine, isoleucine) and aromatic side chains (tyrosine, phenylalanine, tryptophane, histidine).

Protein fragment of the present invention is useful for applications where one or more functional properties of fibronectin are desirable or where modification of one or more signaling properties associated with fibronectin are desirable. For example, protein fragment of the present invention may be employed as a therapeutic to inhibit cell signaling. Antimetastatic effects of protein fragments derived from fibronectin are described for example, in Kato et al., *Clinical Cancer Research*, 8:2455-2462 (2002).

Likewise, surfaces modified using the protein fragment of the present invention are useful for applications where one or more functional properties of fibronectin are desirable or where modification of one or more signaling properties associated with fibronectin are desirable. Such applications include in vitro cell culture as well as fostering cell growth in vivo. For example, prosthetic devices coated with fibronectin are desirable to foster growth and migration of new epithelial tissue. Preparation of fibronectin coated prosthetic devices are well known to one of skill in the art (see, e.g., U.S. Pat. No. 5,171,318).

Surfaces modified with a protein fragment of the present invention may employ either passive (i.e., non-covalent) coating, covalent immobilization of the compound or any other method of deposition of the compound.

Surfaces modified with a protein fragment of the present invention for use in cell culture include cell culture vessels and microcarriers. Suitable cell culture vessels for use in the present invention are well known to one of skill in the art. Examples of suitable vessels include, but are not limited to, dishes, flasks, multi-well plates, and microscopic slides. Microcarriers suitable for cell culture are also well known to one of skill in the art. See, e.g., Nie, *Biotechnol. Prog.*, 25 (1):20-31 (2009).

Advantageously, cells cultured using the surfaces of the present invention are suitable for therapeutic application (e.g., in wound healing) and avoid problems inherent to the use of isolated fibronectin from a different source which may otherwise elicit an immunogenic response and even lead to rejection of transplanted cells.

EXAMPLES

The protein fragment of the present invention having amino acid sequence (SEQ ID NO: 3) was produced using a commercially available service. This protein fragment was then added on a surface to modify the surface. The surface of a cell culture vessel was modified by a protein fragment of the present invention using well established techniques known to a skilled artisan. In brief, covalent immobilization of a protein fragment was done by EDC/NHS Chemistry, protein fragment solution was added onto the surface followed by an incubation and wash step. Alternatively, for passive adsorption of a protein fragment, the protein fragment was diluted in phosphate buffered saline and the resultant solution applied to a tissue culture surface. Incubation was allowed at room temperature for at least 2 hrs after which the surface was washed and the tissue culture surface used. For human embryonic stem cells and induced pluripotent stem cells, tissue culture treated surface was coated for 2 hrs after which the coating was removed prior to seeding cells.

Cell cultures were established based on established protocols are well known to a skilled artisan.

To explore the ability of a surface modified by a protein fragment of the present invention to support cell culture and/or provide one or more functional characteristics of a fibronectin coated surface, cells were seeded and monitored on both such surfaces under the same culture conditions.

In brief, LNCaP cells, bone marrow-derived human mesenchymal stem cells, human embryonic cell line H9 available from ATCC, Lonza, and Wicell were cultured according to supplier's instructions. Likewise, human induced pluripotent stem cells (i.e., GIBCO® [Episomal human induced pluripotent stem cell line]) were cultured according to supplier's instructions.

For cell attachment assays, cells were seeded in serum-free media. For MSC, cells were cultured in Mosaic formulation for MSC culture with media supplied by BD Technologies (BDT). For human embryonic stem cell culture (i.e., H9 cell line and human induced pluripotent stem cells (GIBCO® (Episomal human induced pluripotent stem cell lineD), cells were cultured in STEMPRO® (human embryonic stem cell serum-free media) (Life Technologies) or defined mTeSR1 media (Stem Cell Technologies).

Cell attachment was monitored by visual inspection under the microscope and images captured. Quantification was performed by measuring cell count using techniques well known to a skilled artisan.

Figure 1:
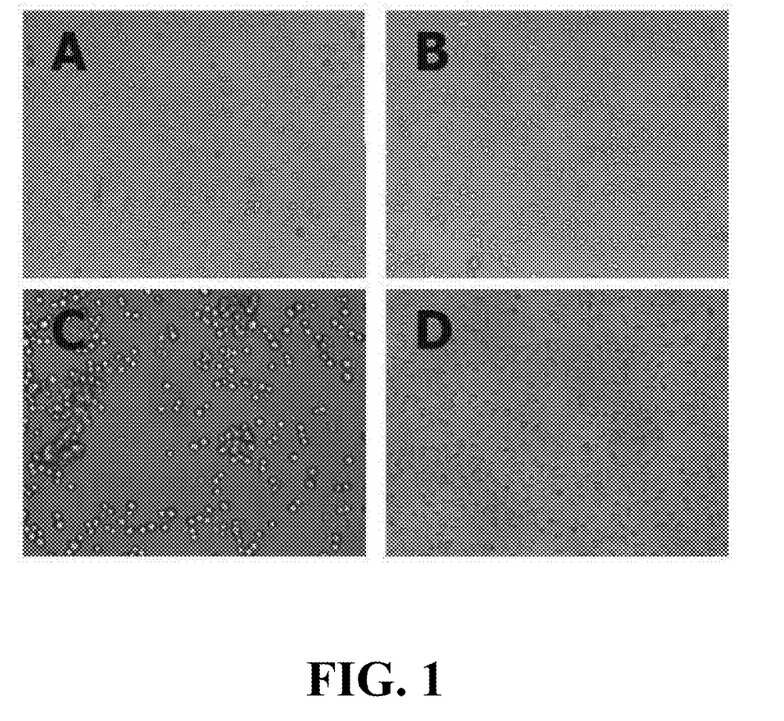
FIG. 1A is an image of LNCaP human prostate cancer cells attached to a surface that is coated by covalent immobilization of a recombinant protein fragment having the amino acid sequence of SEQ ID NO: 3.
FIG. 1B is an image of LNCaP human prostate cancer cells attached to a tissue culture surface that has a coating of human fibronectin thereon.
FIG. 1C is an image of LNCaP human prostate cancer cells present on a tissue culture surface without any extracellular matrix protein coating thereon.
FIG. 1D is an image of LNCaP human prostate cancer cells attached to a tissue culture surface that is passively coated by a recombinant protein fragment having the amino acid sequence of SEQ ID NO: 3.
Figure 2:
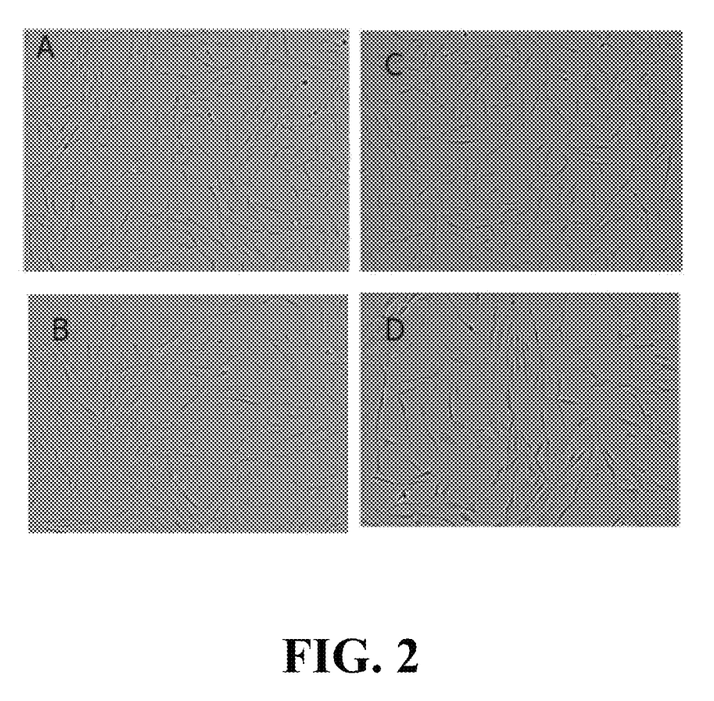
FIGS. 2A and 2B are images of bone marrow-derived human mesenchymal stem cells (MSCs) of either Donor "A" or Donor "B" attached to a tissue culture surface that is coated with human-origin Fibronectin (HFN).
FIGS. 2C and 2D are images of bone marrow-derived human MSCs attached to a tissue culture surface that is coated with a recombinant protein fragment having the amino acid sequence of SEQ ID NO: 3.

As reflected in FIGS. 1A and D, cell attachment and spreading of LNCaP human prostate cancer cells was evident on surfaces coated by either covalent modification or passive adsorption of with a protein fragment having the amino acid sequence of SEQ ID NO: 3. In fact, cell attachment and spreading of LNCaP human prostate cancer cells on surfaces modified with a protein fragment of SEQ ID NO: 3 was comparable to that exhibited on a surface coated with human fibronectin which served as a positive control (see FIG. 1B). In contrast, cell attachment and spreading was significantly reduced in tissue culture surface without a coating thereon which served as a negative control (see FIG. 1C).

Figure 3:
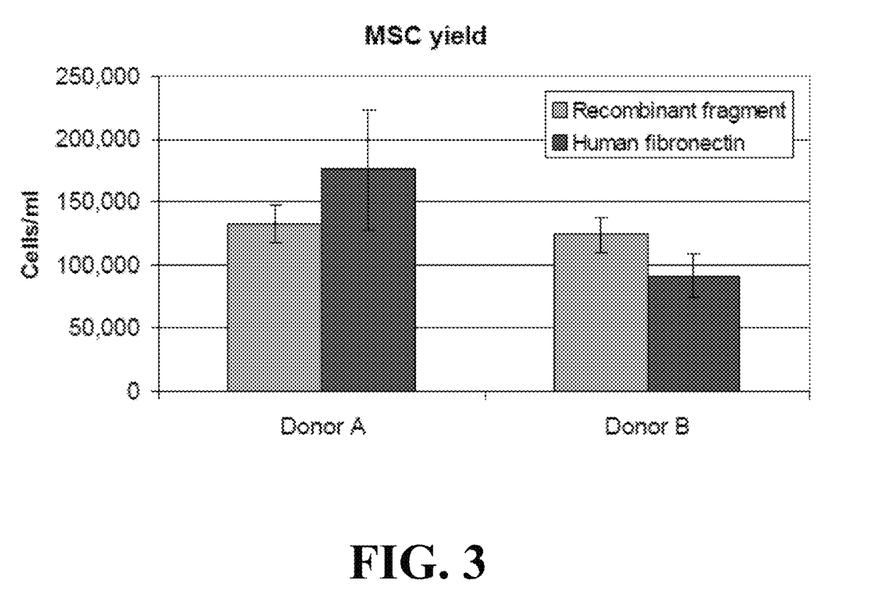
FIG. 3 is a graph of the cell yield of bone marrow-derived human MSCs of either Donor "A" or Donor "B" for passages 2 cultured in Mosiac medium on a tissue culture surface coated with either human-origin Fibronectin or a recombinant protein fragment having the amino acid sequence of SEQ ID NO: 3.

Similarly, surfaces modified by a protein fragment having the amino acid sequence of SEQ ID NO: 3 supported cell attachment and spreading of bone marrow-derived MSCs in a manner comparable to that of a surface coated with human-origin fibronectin as reflected upon a visual inspection (see FIGS. 2A-D). Further, a quantitative analysis of the cell yield of bone-marrow derived MSC from two different donors (Donor "A" and Donor "B") for passages 2 cultured in Mosiac medium on either a surface modified by a protein fragment having the amino acid sequence of SEQ ID NO: 3 or a surface coated with human-origin fibronectin also revealed comparable % cell yield between the different coated surfaces for each donor (see FIG. 3).

Figure 4:
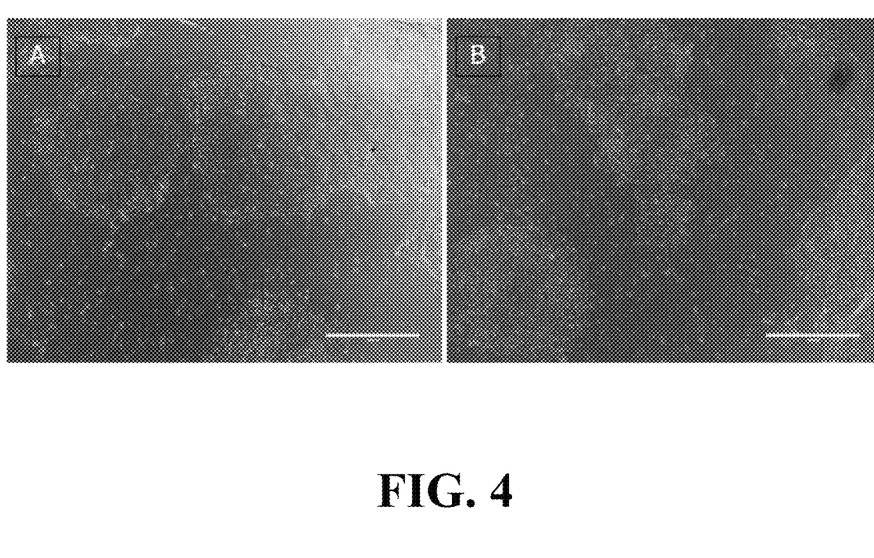
FIGS. 4A and 4B are images of induced pluripotent stem cells (iPSC) cultured in STEMPRO® (serum-free cell culture medium) on a surface coated with either (A) MATRIGEL™ (extracellular matrix) (by Becton, Dickinson & Company) or (B) a recombinant protein fragment having the amino acid sequence of SEQ ID NO: 3.

Additionally, comparable morphology was exhibited by induced pluripotent stem cells cultured in STEMPRO® (serum-free cell culture medium) on a surface coated with MATRIGEL™ (extracellular matrix) or a surface modified with a protein fragment having the amino acid of SEQ ID NO: 3 (see FIGS. 4A and 4B).

Figure 5:
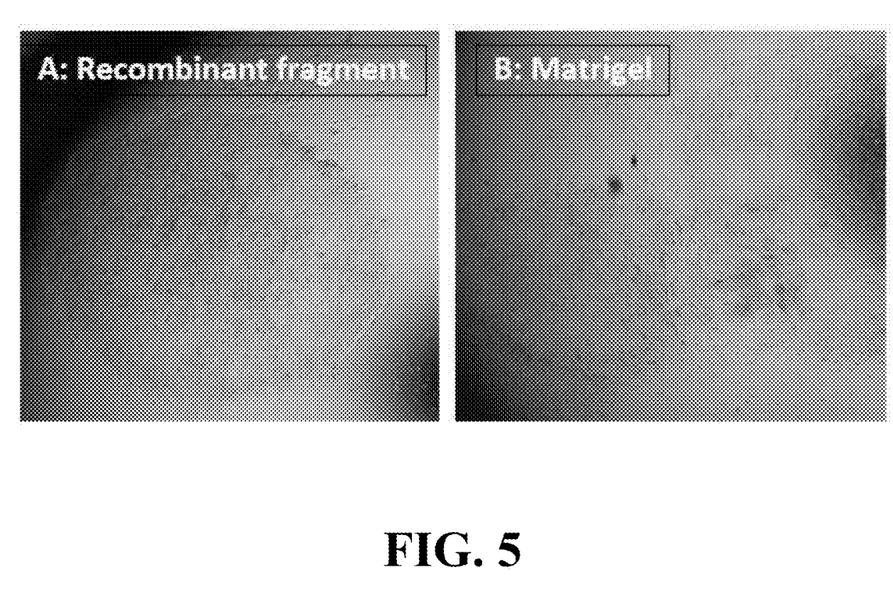
FIGS. 5A and 5B are images of human embryonic cell line H9 cultured in STEMPRO® (serum-free cell culture medium) on a surface coated with either (A) a recombinant protein fragment having the amino acid sequence of SEQ ID NO: 3 or (B) MATRIGEL™ (extracellular matrix).

Likewise, comparable morphology was exhibited by human embryonic stem cell line H9 cultured in STEMPRO® (serum-free cell culture medium) on a surface modified with a protein fragment having the amino acid of SEQ ID NO: 3 or a surface coated with MATRIGEL™ (extracellular matrix) (see FIGS. 5A and 5B).

Figure 6:
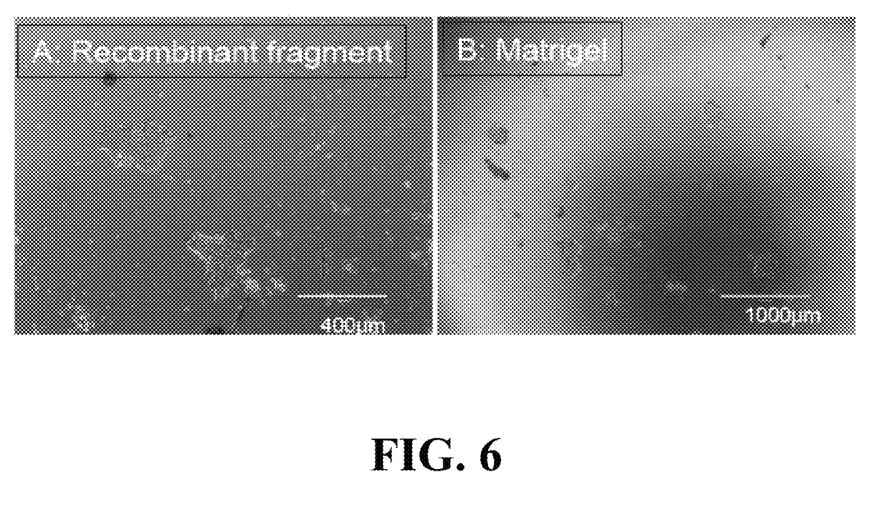
FIGS. 6A and 6B are images of induced pluripotent stem cells (iPSC) cultured in mTeSR1 media on a surface coated with either (A) a recombinant protein fragment having the amino acid sequence of SEQ ID NO: 3 or (B) MATRIGEL™ (extracellular matrix).

Similarly, comparable morphology was exhibited by induced pluripotent stem cells cultured in mTeSR1 media on a surface modified with a protein fragment having the amino acid of SEQ ID NO: 3 or a surface coated with MATRIGEL™ (extracellular matrix) (see FIGS. 6A and 6B).

It will be appreciated by those skilled in the art that changes could be made to the embodiments described above without departing from the broad inventive concept thereof. It is understood, therefore, that this invention is not limited to the particular embodiments disclosed, but is intended to cover modifications that are within the spirit and scope of the invention, as defined by the appended claims.

What is claimed is:

1. A method of culturing cells comprising culturing the cells on a surface wherein at least a portion of the surface is modified with a protein fragment comprising amino acid sequence PLS PPTNLHLEAN PDTGVLTVSW ERSTTP­DITG YRITTTPTNG QQGNSLEEVV HADQSSCTFD NLSPGLEYNV SVYTVKDDKE SVPISDTIIP AVPPPT­DLRF TNIGPDTMRV TWAPPPSIDL TNFLVRYSPV KNEEDVAELS ISPSDNAVVL TNLLPGTEYV VSVSS­VYEQH ESTPLRGRQK TGLDSPTGID FSDITANSFT VHWIAPRATI TGYRIRHHPE HFSGRPREDR VPHSRN­SITL TNLTPGTEYV VSIVALNGRE ESPLLIGQQS TVS­DVPRDLE VVAATPTSLL ISWDAPAVTV RYYRITYGET GGNSPVQEFT VPGSKSTATI SGLKPGVDYT ITVYAVT­GRG DSPASSKPIS INYRT (SEQ ID NO: 1); wherein the cells are cultured in serum-free media.

2. The method of claim 1 wherein the cells are derived from a human.

3. The method of claim 1, wherein the cells are LNCaP cells, bone marrow-derived mesenchymal stem cells, embryonic cell line H9 or induced pluripotent stem cells.

4. The method of claim 1, wherein said cells are embryonic stem cells.

5. A cell culture vessel or microcarrier comprising a surface, wherein at least a portion of the surface is modified with a protein fragment comprising amino acid sequence MHHH­HHHPLS PPTNLHLEAN PDTGVLTVSW ERSTTPDITG YRITTTPTNG QQGNSLEEVV HADQSSCTFD NLSPG­LEYNV SVYTVKDDKE SVPISDTIIP AVPPPTDLRF TNIGPDTMRV TWAPPPSIDL TNFLVRYSPV KNEED­VAELS ISPSDNAVVL TNLLPGTEYV VSVSSVYEQH ESTPLRGRQK TGLDSPTGID FSDITANSFT VHWIAP­RATI TGYRIRHHPE HFSGRPREDR VPHSRNSITL TNLTPGTEYV VSIVALNGRE ESPLLIGQQS TVSD­VPRDLE VVAATPTSLL ISWDAPAVTV RYYRITYGET GGNSPVQEFT VPGSKSTATI SGLKPGVDYT ITVYAVT­GRG DSPASSKPIS INYRT (SEQ ID NO: 3).

6. The cell culture vessel or microcarrier of claim 5, wherein the cell culture vessel is a dish, a flask, a multi-well plate, or a microscopic slide.

7. A method of culturing cells comprising culturing the cells on a surface wherein at least a portion of the surface is modified with a protein fragment comprising amino acid sequence MHHHHHHPLS PPTNLHLEAN PDTGV­LTVSW ERSTTPDITG YRITTTPTNG QQGNSLEEVV HADQSSCTFD NLSPGLEYNV SVYTVKDDKE SVPIS­DTIIP AVPPPTDLRF TNIGPDTMRV TWAPPPSIDL TNFLVRYSPV KNEEDVAELS ISPSDNAVVL TNLL­PGTEYV VSVSSVYEQH ESTPLRGRQK TGLDSPTGID FSDITANSFT VHWIAPRATI TGYRIRHHPE HFSGR­PREDR VPHSRNSITL TNLTPGTEYV VSIVALNGRE ESPLLIGQQS TVSDVPRDLE VVAATPTSLL ISWDA­PAVTV RYYRITYGET GGNSPVQEFT VPGSKSTATI SGLKPGVDYT ITVYAVTGRG DSPASSKPIS INYRT (SEQ ID NO: 3).

8. The method of claim 7, wherein the cells are derived from a human.

9. The method of claim 7, wherein said cells are embryonic stem cells.

10. The method of claim 8, wherein said cells are embryonic stem cells.

11. The method of claim 7, wherein said cells are LNCaP cells.

12. The method of claim 7, wherein said cells are bone marrow-derived human mesenchymal stem cells.

13. The method of claim 7, wherein said cells are human embryonic cell line H9.

14. The method of claim 7, wherein said cells are induced pluripotent stem cells.

15. The method of claim 7, wherein said cells exhibit comparable or improved cell attachment as compared to a surface coated with fibronectin of human-origin.

* * * * *